(12) United States Patent
Haras et al.

(10) Patent No.: US 8,538,506 B2
(45) Date of Patent: Sep. 17, 2013

(54) IMAGING DEVICE AND METHOD FOR OPERATING AN IMAGING DEVICE

(75) Inventors: Gabriel Haras, Mücke (DE); Ute Feuerlein, Erlangen (DE); Matthias Niethammer, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 773 days.

(21) Appl. No.: 11/655,179

(22) Filed: Jan. 19, 2007

(65) Prior Publication Data

US 2007/0189445 A1  Aug. 16, 2007

(30) Foreign Application Priority Data

Jan. 20, 2006 (DE) .......................... 10 2006 002 896

(51) Int. Cl.
*A61B 6/03* (2006.01)
(52) U.S. Cl.
USPC ............ 600/431; 600/407; 600/420; 600/458
(58) Field of Classification Search
USPC .................................. 600/407, 420, 458, 431
See application file for complete search history.

(56) References Cited

U.S. PATENT DOCUMENTS

| | | | |
|---|---|---|---|
| 5,459,769 A * | 10/1995 | Brown ............................... 378/4 |
| 5,583,902 A * | 12/1996 | Bae ................................... 378/8 |
| 5,687,208 A | 11/1997 | Bae et al. |
| 6,188,744 B1 * | 2/2001 | Shinohara et al. ................. 378/8 |
| 6,236,878 B1 * | 5/2001 | Taylor et al. .................. 600/416 |
| 6,385,483 B1 * | 5/2002 | Uber et al. ..................... 600/431 |
| 6,535,821 B2 * | 3/2003 | Wang et al. ..................... 702/19 |
| 6,795,524 B2 * | 9/2004 | Hayashi ..................... 378/98.12 |
| 2002/0114503 A1 * | 8/2002 | Klotz et al. .................... 382/131 |
| 2004/0172303 A1 * | 9/2004 | Declerck et al. .................. 705/2 |
| 2007/0238956 A1 * | 10/2007 | Haras et al. ................... 600/407 |

FOREIGN PATENT DOCUMENTS

DE 696 31 607 T2 12/2004

* cited by examiner

*Primary Examiner* — Tse Chen
*Assistant Examiner* — Vani Gupta
(74) *Attorney, Agent, or Firm* — Harness, Dickey & Pierce, P.L.C.

(57) ABSTRACT

An imaging device is disclosed for generating successive tomograms of an object. In at least one embodiment, the imaging device includes a radiation source, a detector, a positioning unit and a control unit for controlling the positioning unit and for evaluating the recorded data of the detector. In at least one embodiment, it is provided that the control unit is set up for matching a contrast medium protocol, in which parameters for contrast medium administration are stored, provided for examinations in a contrast medium device, to a scan protocol provided for the examination, in which operating parameters for generating successive tomograms are stored, for preventing unnecessary administration phases. This provides for a contrast medium examination with the least possible contrast medium administration.

16 Claims, 1 Drawing Sheet

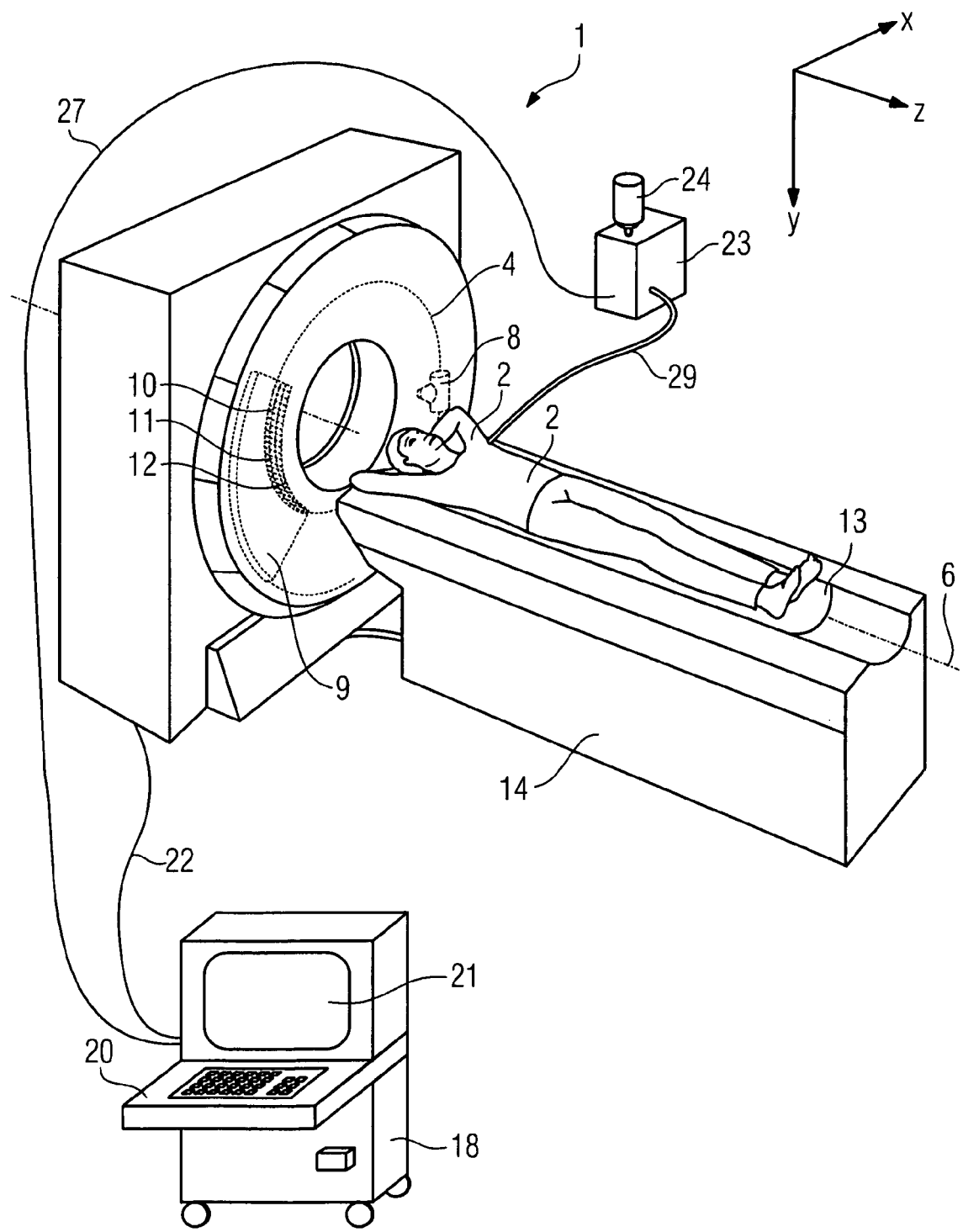

IMAGING DEVICE AND METHOD FOR OPERATING AN IMAGING DEVICE

PRIORITY STATEMENT

The present application hereby claims priority under 35 U.S.C. §119 on German patent application number DE 10 2006 002 896.1 filed Jan. 20, 2006, the entire contents of which is hereby incorporated herein by reference.

FIELD

Embodiments of the invention generally relate to an imaging device for generating successive tomograms of an object. Embodiments of the invention also generally relate to a method for operating such an imaging device.

BACKGROUND

An imaging device for generating successive tomograms is used for obtaining information about the interior of the object examined. From the tomograms, valuable information about the position, the size or the structure of internal organs, of bone tissue or other soft tissue of a patient can be obtained, for example. In particular, the successive tomograms can also be recalculated in a three-dimensional representation.

Such an imaging device for recording successive tomograms can be, for example, an X-ray computer tomograph, a magnetic resonance tomograph, a photon emission computer tomograph or a positron emission tomograph. By the same token, such an imaging device can be constructed on the basis of ultrasound.

The contrast of the images of the object such as, for example of a patient, generated by such an imaging device, is produced by locally different properties of excitation, absorption, reflection or emission of the examined material compared with the radiation, particle radiation or sound waves used by the imaging device. In the case of an X-ray device, the different absorption or attenuation characteristics of different types of tissue are used for producing contrast. Since, for example, bone tissue and soft tissue differ greatly in the said characteristics, it is possible to analyze the structure of a bone of a patient on the basis of the associated contrast in the images.

Organs or vessels which do not significantly differ in the said characteristics for forming a contrast in the recorded images of surrounding tissue cannot be examined in a conventional manner due to the resultant contrast which is too low. When examining an organ through which blood circulates, for example a heart, a liver or a vessel in the area of the extremities of the patient, therefore, a contrast medium is introduced into the circulatory system of the patient before beginning the examination with the imaging device. As a consequence of the contrast medium, the examined organs are imaged with sufficiently high contrast compared with the surrounding tissue.

When generating tomograms with contrast medium administration, attention must be paid to the simultaneous presence of the contrast medium. For this purpose, it is becomes necessary to match the operating parameters of the imaging device and the propagation of the administered contrast medium in the patient to one another. For this purpose, a so-called scan protocol, in which operating parameters of the imaging device are stored for image recording, and a so-called contrast medium protocol in which parameters of a contrast medium administration are stored, are in each case selected matching one another for a desired area of examination.

In a scan protocol, for example, power values, the duration of the acting radiation, the radiation energy, a feed rate or a scan delay time, i.e. a delay time between individual tomogram recordings or between a monitoring and a recording phase are stored as operating parameters.

During the examination, the contrast medium is administered in accordance with the contrast medium protocol selected for the scan protocol, for example by means of a contrast medium device. Parameters for administering the contrast medium can be, for example, the concentration, the flow or the absolute quantity of contrast medium to be supplied. In particular, a contrast medium protocol can comprise a number of different administration phases which differ in the said parameters but also in the type of medium to be supplied. In complex contrast medium protocols, phases in which, for example, a sodium chloride solution is supplied, can also be arranged between phases in which contrast medium is administered.

The contrast medium protocol is used for generating a predictable contrast medium course in the patient so that during the recording of the successive tomograms, the contrast medium concentration required in each case for forming contrast is present in the area of examination. For example, a phase in which a sodium chloride solution is supplied is used for predictably stopping the course of contrast medium in time without loading the patient with too much contrast medium in an undesirable manner.

In practice, it disadvantageously frequently happens that contrast medium is still administered in accordance with the contrast medium protocol when this would no longer be necessary for recording the tomograms. This unwanted administration of additional quantity is of no additional use to the patient.

SUMMARY

In at least one embodiment of the invention, an imaging device is specified for generating successive tomograms of an object which, during a contrast medium examination allows the organs to be examined to be represented with good contrast with the least possible quantity of contrast medium to be administered. In at least one embodiment of the invention, a method is specified for operating the imaging device which is associated with the same advantages.

According to at least one embodiment of the invention, the object directed at a device is achieved by way of an imaging device for generating successive tomograms of an object with a radiation source, with a detector, with a positioning unit and with a control unit for controlling the positioning unit and for evaluating the recorded data of the detector, the control unit being set up for matching a contrast medium protocol in which parameters for contrast medium administration are stored, intended for examination on a contrast medium device, to a scan protocol provided for the examination, in which operating parameters for generating the successive tomograms are stored, avoiding unnecessary administration phases.

In a first step, at least one embodiment of the invention is based on the consideration that unnecessary contrast medium is administered due to a lack of correlation between the scan protocol and the contrast medium protocol. Thus, it happens, for example, that a contrast medium or a sodium chloride solution is administered without any use even after the end of scanning of the imaging device. As well, contrast medium administered before the end of scanning can frequently no longer reach the location of examination before the conclusion of the scan protocol if the location of examination is remote from the location of administration of the contrast medium.

In a second step, at least one embodiment of the invention is based on the consideration that an unnecessarily administered additional quantity of contrast medium can be avoided if the contrast medium protocol is correspondingly matched to the scan protocol provided for the examination. For the matching, both the duration of the protocols in time can be adapted to one another and the parameters of the contrast medium administration in the contrast medium protocol can be changed. In particular, the concentration to be administered, the quantity or the flow of the medium can thus be changed in the individual administration phases of the contrast medium protocol. Matching the contrast medium protocol also includes the addition of new administration phases or the deletion of administration phases already existing. Furthermore, the time of switching between the administration of the contrast medium and the administration of a further medium such as, e.g. a sodium chloride solution can also be moved.

If, for example, the contrast medium administration is replaced by a sodium chloride solution at a suitable time in a given administration phase of the contrast medium protocol, the contrast medium bolus as such can be retained for the examination therein, wherein, after the end of the examination, the subsequent sodium chloride solution and not expensive and stressful contrast medium flows through the location of examination. In particular, such a subsequent sodium chloride solution is called a so-called bolus chaser.

For the matching, the control unit derives, for example, from the individual phases of the protocols whether there are unnecessary administration phases for the contrast medium. For this purpose, the rate of propagation of the contrast medium, the location of examination, the intended scanning rate, a device-specific or adjusted delay time during or at the recording of the tomograms can be taken into consideration. The parameters taken into consideration can be based on measurement values or on empirical values and, in particular, can also be dependent on the constitution of the patient. The contrast medium protocol is then correspondingly adapted so that such unnecessary administration phases in the contrast medium administration are prevented.

The control unit is advantageously set up for determining, before the beginning of the examination, a conflict situation between scan protocol and contrast medium protocol and specifying a corresponding warning dialog with a request for matching if an unnecessary administration phase is determined. For this purpose, the warning dialog can be output, for example, on a graphical display unit. A conflict situation exists, for example, if, according to the contrast medium protocol, contrast medium is still supplied after the end of scanning. In particular, it is possible to propose alternatives to the further procedure to the user. Thus, for example, he can use the intended contrast medium protocol for the examination in spite of the existing conflict. As an alternative, he could also propose an altered, particularly abbreviated contrast medium protocol.

In an advantageous embodiment of the invention, the control unit can be connected to the contrast medium device for driving, and is set up for matching the contrast medium protocol automatically to the scan protocol, particularly during the examination. Connection of the control unit to the contrast medium device allows automatic adaptation of the contrast medium protocol, for example during a conflict situation which has been found. In particular, the control unit can drive the contrast medium device in such a manner that the contrast medium protocol is automatically matched to the scan protocol during the examination. In this connection, it may be possible to take into consideration for the matching delay times etc. when carrying out the real examination.

In a further advantageous embodiment, the control unit is set up for extending, shortening or newly generating an administration phase as parameter of the contrast medium administration. This allows unnecessary contrast medium administrations to be avoided.

The control unit is suitably set up for stopping the contrast medium protocol immediately before or on reaching the end of the scan protocol. If the contrast medium administration is stopped on reaching the end of the scan protocol at the latest, any additional unnecessary contrast medium or sodium chloride administration is prevented. The medium administered after the end of the scan protocol has no longer any effect for imaging.

The other alternative takes into consideration the fact that the contrast medium administration can be stopped even before the end of the scan protocol is reached. This is due to the rate of propagation of the contrast medium administered. If this is known or is estimated, it is possible to precalculate what time an administered contrast medium will need for reaching the location of examination. The contrast medium administration can be stopped shortened by this delay time even before reaching the end of the scan protocol. In an advantageous embodiment, the control unit is set up for taking into consideration, for calculating the matching or stopping time preceding the end of scanning, operating parameters from the scan protocol, particularly a scan delay time, i.e. a device-specific or adjusted delay time between individual tomogram recordings or between a monitoring and a recording phase. The administration of the contrast medium can be stopped, in particular, by shortening in advance an administration phase of the contrast medium protocol.

Instead of stopping the contrast medium administration, the contrast medium protocol can be adapted by administration of a bolus chaser immediately before or on reaching the end of scanning. At the latest on reaching the end of scanning or correspondingly shortened by the abovementioned delay time, a medium which does not stress the patient, e.g. a sodium chloride solution, can be administered instead of the contrast medium in the corresponding administration phase. As a result, the preceding contrast medium retains its distribution function so that no impairment of the image contrasts can be expected in the tomograms created.

The end of scanning itself is advantageously calculated from the operating parameters. If, for example, the location of examination and the scanning rate of the imaging device are predetermined, the scanning period, and thus the end of scanning can possibly be determined by taking into consideration the scanning delay time. In particular, the scanning period can be compared with the duration of the contrast medium protocol.

The control unit is also suitably set up for calculating a matching or stopping time, preceding the end of scanning, from a rate of propagation of the contrast medium and a position of the area of examination relative to the location of the contrast medium administration. For this purpose, the rate of propagation of the contrast medium is determined, for example, via a test bolus course preceding the actual examination. For this purpose, the arrival of the slightly administered contrast medium is measured in advance at various locations of the patient, for example by image evaluation, and from this the rate of propagation is determined.

In particular, this embodiment is also applicable if the imaging device operates in so-called bolus tracking mode. For this purpose, a series of successive tomograms is determined at a fixed scanning position preceding the field of examination before starting the actual examination and the contrast of the tomograms is evaluated in selected image areas. In this manner, the arrival time of the administered contrast medium can be determined directly and, triggered by this, the examination can be started thereafter at an optimum time. From the arrival time, the rate of propagation can be derived, in turn.

The further distant the field of examination from the location of contrast medium administration, the earlier the contrast medium protocol can be stopped or modified, with respect to the end of scanning. In particular, in the case of a predetermined rate of propagation of the contrast medium which was measured, for example, or is based on empirical values, a correction factor can be implemented which takes into consideration the distance of the field of examination from the location of the contrast medium administration. The precalculated time of the end of scanning is shortened by this correction factor and the contrast medium administration is stopped in advance or a bolus chaser is administered instead of the contrast medium.

The position of the field of examination can be advantageously derived from the position of the positioning unit. With a fixed predetermined position of the patient relative to the positioning unit, the position of the field of examination can be derived from the position of the positioning unit. As an alternative, the field of examination can be picked up from the recorded tomograms by means of image processing. For this purpose, for example, recorded organs can be automatically detected and from these the position of the field of examination can be derived.

According to at least one embodiment of the invention, a method is disclosed for operating an imaging device with a radiation source, with a detector and with a positioning unit, wherein a contrast medium protocol, in which parameters for contrast medium administration are stored and which is intended for examination on a contrast medium device is matched to a scan protocol provided for examination in which operating parameters for generating successive tomograms are stored, to prevent unnecessary administration phases.

Further advantageous embodiments of the method are found in the text below directed to a method. In this context, the advantages mentioned for embodiments of the imaging device should be correspondingly adopted for embodiments of the corresponding method.

BRIEF DESCRIPTION OF THE DRAWINGS

Example embodiments of the invention are explained in greater detail with reference to a drawing, in which:

FIG. 1 shows an x-ray computer tomograph with associated control unit in a perspective representation as an imaging device.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows as imaging device a computer tomograph 1 for examining an object, in this case a patient 2. The computer tomograph 1 comprises a radiation source 8, arranged rotatably around an axis of rotation 6 in a gantry 4 for emitting x-ray radiation. Opposite the radiation source 8, an arched detector 9 is arranged which comprises a number of detector elements arranged in a row of detectors 10, 11, 12.

The computer tomograph 1 also includes a table top 13 which is mounted displaceably on a table 14 along the axis of rotation 6.

As a further component of the computer tomograph 1, a control unit 18 can be seen which has an operating console 20 and a graphical display unit 21. The control unit 18 is connected to the computer tomograph 1 via a control line 22.

The control unit 18 is set up for driving the advance of the moving table top 13 and the rotation of the gantry 4 for recording successive tomograms. Gantry 4 and table top 13 together form a positioning unit which enables tomograms to be recorded at different spatial positions of the patient 2. The scanning rate of the computer tomography 1 can be adjusted via the pitch value, i.e. the ratio of speed of rotation of the gantry 4 and advancing rate of the table top 13. The rotation of the gantry 4 ensures in this case that a tomogram will be recorded on a longitudinal position of the patient 2, whereas the advance of the table top 13 is responsible for the sequence of tomograms to be recorded.

To acquire a tomogram, the x-radiation emitted by the radiation source 8 and passing through the patient 2 is detected by use of the detector 9. In the computer tomograph 1 shown, the radiation source 8 generates a fan-shaped x-ray beam for this purpose. In each position of the gantry 4, a characteristic attenuation image of the x-radiation is thus detected. From the projections obtained in various positions of the gantry 4, a tomogram is reconstructed on which tissues having different attenuation characteristics are represented with different gray scale values.

The tomograms are recorded by driving the gantry 4, the table top 13 and the radiation source 8 by way of scan protocols selected at the control unit 18. In the scan protocols, power values for the radiation source 8, feed parameters such as, in particular, a pitch value, and a scan delay value are stored.

For the examination of organs filled with blood, for example a heart, a liver or a blood vessel, a contrast medium administration is provided. For this purpose, the control unit 18 is connected via a control line 27 to a contrast medium device 23 via which a contrast medium 24 is supplied under control to the patient 2 by means of a contrast medium hose 29 in accordance with a predetermined contrast medium protocol. The respective contrast medium protocol comprises as parameters of the contrast medium administration, in particular, the number and type of different administration phases which in each case differ in the type of medium supplied, its flow and the absolute quantity.

At the beginning of the examination, the control unit 18 checks the extent to which a conflict with respect to unnecessary administration phases exists between the selected scan protocol and the selected contrast medium protocol. For this purpose, the control unit 18 checks, in particular, whether contrast medium 24 is still administered according to the contrast medium protocol when the end of scanning is reached. For this purpose, the end of scanning is precalculated from the operating parameters according to the scan protocol. If it is found that contrast medium 24 is still unnecessarily administered at the end of scanning, a dialog is output on the display unit 21 by which the user is notified that, with the contrast medium protocol provided, contrast medium 24 is still administered after the end of scanning. The user can then decide by way of an input whether he wishes to use the intended contrast medium protocol for the examination or whether the intended contrast medium protocol is automatically shortened by the control unit 18.

If the user selects automatic shortening by the control unit 18, the latter initially shortens the contrast medium protocol in such a manner that the contrast medium administration is stopped at the end of the scan time in the last administration phase.

The examination in the intended field of examination is triggered by image evaluations of a scanning position preceding the field of examination. For this purpose, the computer tomograph 1 records a series of tomograms at the preceding scanning position. In a selected image area, particularly with a vessel, the recorded attenuation values are added and a mean value is determined. When the contrast medium 24 arrives, the attenuation values increase so that, when a predetermined threshold value is exceeded, the arrival of the contrast medium 24 at the scanning position can be determined. If the threshold value is exceeded, the control unit 18 interrupts the monitoring action of the computer tomograph 1 and controls the positioning unit 4, 13 in such a manner that the recording of the successive tomograms according to the scan protocol can begin in the field of examination. From the difference between the administration time and the arrival time of the contrast medium in the preceding scanning position, the control unit 18 determines a rate of propagation of the contrast medium 24 in the patient 2.

From the current position of the positioning unit 4, 13, the control unit 18 also detects the distance of the field of examination from the location of the contrast medium administration. If the end of scanning is reached, the control unit 18 calculates from the rate of propagation of the contrast medium 24 and the distance of the contrast medium administration from the field of examination a correction time which is subtracted from the precalculated time at the end of scanning. The contrast medium administration is stopped shortened by this time before the end of scanning is reached.

In an alternative embodiment, the contrast medium protocol is modified, taking into consideration the correction time determined, in such a manner that the contrast medium device 23 switches from contrast medium administration to the supply of a sodium chloride solution shortened by the correction time before the end of scanning. In this arrangement, the sodium chloride solution acts as so-called bolus chaser, the course of contrast medium in the patient 2 until the recording of successive tomograms is ended remaining unaffected. The patient 2 is not unnecessarily stressed by contrast medium administration.

The procedure described can also take place in individual scanning phases of the scan protocol and is not restricted to the end of examination in general.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging device for generating successive tomograms of an object, comprising:
    a radiation source;
    a detector;
    a positioning unit; and
    a control unit configured to control the positioning unit and to evaluate the recorded data of the detector, the control unit being configured to match a contrast medium protocol, in which parameters for contrast medium administration are stored, intended for use in an examination by a contrast medium device, to a scan protocol provided for the examination, in which operating parameters for generating the successive tomograms are stored, avoiding unnecessary administration phases, wherein
        the control unit is configured to match the contrast medium protocol automatically to the scan protocol,
        the control unit is configured to determine, before the beginning of the examination, a conflict situation between scan protocol and contrast medium protocol relating to different time durations for the scan and contrast medium protocols,
        the examination includes all of the tomograms generated by the imaging device of the object such that none of the tomograms of the object are generated prior to the control unit determining the conflict situation, the control unit is configured to drive the contrast medium device, and the control unit is configured to, detect a distance of the field of examination from the location of a contrast medium administration, calculate a correction time based on a rate of propagation of the contrast medium and the detected distance if the end of scanning is reached, shorten the contrast medium administration based on the calculated correction time, and stop the contrast medium protocol immediately before or on reaching the end of the scan protocol.

2. The imaging device as claimed in claim 1, wherein the control unit is set up for stopping the contrast medium protocol by shortening an administration phase.

3. The imaging device as claimed in claim 1, wherein the control unit is set up for adapting the contrast medium protocol at least one of immediately before and on reaching the end of scanning by administering a bolus chaser.

4. The imaging device as claimed in claim 1, wherein the control unit is set up for calculating the end of scanning from the operating parameters.

5. The imaging device as claimed in claim 1, wherein the control unit is set up for calculating a matching or stopping time preceding the end of scanning from the operating parameters.

6. The imaging device as claimed in claim 1, wherein the control unit is set up for calculating a matching or stopping time preceding the end of scanning from a rate of propagation of the contrast medium and the position of the field of examination relative to the location of the contrast medium administration.

7. The imaging device as claimed in claim 6, wherein the control unit is set up for at least one of deriving the position of the field of examination from the position of the positioning unit and detecting the position of the field of examination by image processing.

8. A method for operating an imaging device including a radiation source, a detector and a positioning unit, the method comprising:

matching a contrast medium protocol, in which parameters for contrast medium administration are stored and intended for use in an examination by a contrast medium device, to a scan protocol provided for the examination, in which operating parameters for generating successive tomograms are stored, preventing unnecessary administration phases, wherein the matching automatically adapts the contrast medium protocol to the scan protocol, the matching determines, before the beginning of the examination, a conflict situation between scan protocol and contrast medium protocol relating to different time durations for the scan and contrast medium protocols, and outputs to a display unit a corresponding warning dialog with a request for the matching, the matching detects a distance of the field of examination from the location of a contrast medium administration, the matching calculates a correction time based on a rate of propagation of the contrast medium and the detected distance if the end of scanning is reached, the matching shortens the contrast medium administration based on the calculated correction time, the examination includes all of the tomograms generated by the imaging device of the object such that none of the tomograms of the object are generated prior to the matching determining the conflict situation, and the contrast medium protocol is stopped at least one of immediately before and on reaching the end of the scan protocol.

9. The method as claimed in claim 8, wherein the contrast medium protocol is stopped by shortening an administration phase.

10. The method as claimed in claim 8, wherein the contrast medium protocol is adapted by administering a bolus chaser at least one of immediately before and on reaching the end of scanning.

11. The method as claimed in claim 8, wherein the end of scanning is calculated from the operating parameters.

12. The method as claimed in claim 8, wherein at least one of a matching and stopping time preceding the end of scanning is calculated from the operating parameters.

13. The method as claimed in claim 8, wherein at least one of a matching and stopping time preceding the end of scanning is calculated from a rate of propagation of the contrast medium and the position of the field of examination relative to the location of the contrast medium administration.

14. The method as claimed in claim 13, wherein the position of the field of examination is at least one of derived from the position of the positioning unit and detected by image processing.

15. The imaging device as claimed in claim 1, wherein the control unit is set up for matching the contrast medium protocol automatically to the scan protocol during the examination.

16. The imaging device as claimed in claim 1, wherein the control unit is set up for adapting the contrast medium protocol immediately before or on reaching the end of scanning by administering a bolus chaser.

* * * * *